US006008185A

United States Patent [19]

[11] Patent Number: 6,008,185

[45] Date of Patent: Dec. 28, 1999

Bertram et al.

[54] MACROCYCLIC LACTONES AS MUSK FRAGRANCE ENHANCERS

[75] Inventors: Heinz-Jürgen Bertram, Berkeley Heights, N.J.; Oskar Koch, Göttingen, Germany; Peter Wörner; Horst Surburg, both of Holzminden, Germany

[73] Assignee: Haarmann & Reimer GmbH, Holzminden, Germany

[21] Appl. No.: 09/033,336

[22] Filed: Mar. 2, 1998

[30] Foreign Application Priority Data

Mar. 5, 1997 [DE] Germany ............................ 197 08 924

[51] Int. Cl.[6] ............................ H61K 7/46; C07D 313/00

[52] U.S. Cl. ............................................... 512/12; 549/266

[58] Field of Search ................................ 549/266; 512/12

[56] References Cited

U.S. PATENT DOCUMENTS

| | | | |
|---|---|---|---|
| 3,856,815 | 12/1974 | Hopp et al. | 266/533 |
| 3,890,353 | 6/1975 | Becker | 260/343 |
| 5,319,104 | 6/1994 | Hopp et al. | 549/222 |

FOREIGN PATENT DOCUMENTS

| | | |
|---|---|---|
| 0 424 787 B1 | 10/1996 | Germany . |
| WO 97/32948 | 9/1997 | WIPO . |

OTHER PUBLICATIONS

Sugimara et al., Nippon Kagaku Kaishi, 3:425 (1985).

AG Cameron et al., J. Chem. Soc., Perkin Trans. I, 161 (1986).

R.L. Funk et al., Tetrahedron 42 (1986), 42:2831 (1986).

S.L. Schreiber et al., J. Am. Chem. Soc. 102, 6165 (1980).

Kostova et al., Helv. Chim. Acta 78:440 (1995).

Kalina Kostova et al., "Synthese von Tetradecano–14–lacton durch Ringerweiterung" *Helvetica Chimica Acta,* vol. 78, pp. 440–446 (1995).

*Primary Examiner*—John Kight
*Assistant Examiner*—Raymond Covington
*Attorney, Agent, or Firm*—Brinks Hofer Gilson & Lione

[57] ABSTRACT

Compounds of the formulae

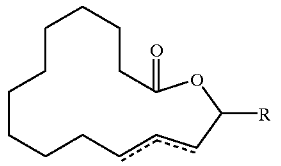

and/or

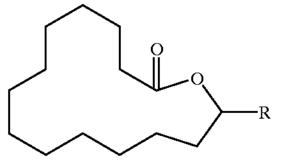

in which

R is hydrogen or methyl, and the dashed lines represent an additional bond in the 11- or 12-position, have extraordinary olfactory properties.

4 Claims, No Drawings

MACROCYCLIC LACTONES AS MUSK FRAGRANCE ENHANCERS

The invention relates to the use of macrocyclic lactones as fragrances.

BACKGROUND OF THE INVENTION

As is known, musk is rare and expensive. Perfumes having a musky scent which are more readily available are therefore sought-after components for the perfume industry. 15-Pentadecanolide of the formula (I)

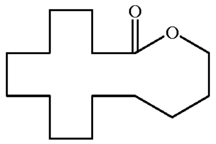

is a constituent of angelica root oil and has a delicate musky scent and the ability to act as a fixative. There have therefore already been intensive efforts to prepare such macrocyclic lactones. The most important syntheses at present start from 13-oxabicyclo [10.4.0]hexadec-1(12)ene, which can be prepared, for example, by free-radical addition of allyl alcohol onto cyclododecanone and acid-catalysed dehydration of the resulting 2-(γ-hydroxypropyl)-cyclododecanone (DE-B 21 36 496)U.S. Pat. No. 3,856,815.

In another process, hydrogen peroxide or alkyl peroxide is added onto 13-oxabicyclo [10.4.0]hexadec-1(12)ene in the presence of sulphuric acid. Thermal or UV-initiated cleavage of the resulting 12-hydroperoxy-13-oxabicyclo [10.4.0]hexadecane (III) gives 15-pentadecanolide (I) and 15-pentadecenolides, which can be hydrogenated to give I (DE-B 2 026 056).

According to Russian Inventor's Certificate 1 133 274, 12-oxo-15-pentadecanolide is reduced in the presence of Raney nickel to give 12-hydroxy-15-pentadecanolide, which is then dehydrated, for example in the presence of phosphoric acid, to give the corresponding 15-pentadec-11- and -12-enolides, and these products are then hydrogenated in the presence of a nickel catalyst to give I.

Surprisingly, it has been found that tetradecenolides whose C=C double bonds are in the 11- or 12-position and the corresponding saturated compounds have valuable organoleptic properties.

DESCRIPTION OF THE PREFERRED EMBODIMENTS

The invention thus provides for the use of compounds of the formulae (II)

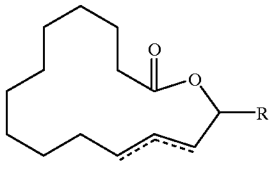

and/or

-continued (III)

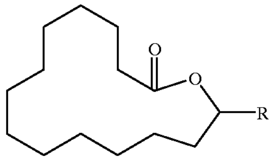

in which

R is hydrogen or methyl, and the dashed lines indicate an additional bond in the 11- or 12-position, as fragrances.

Lactones II and thus also III can be prepared in different ways. For example, they can be prepared by a metathesis reaction on nickel catalysts (S. Inoue et al; Nippon Kagaku Kaishi (1985), 425), by a Claisen rearrangement (D. W. Knight et al., J. Chem. Soc., Perkin Trans. I (1986), 161; R. L. Funk et al., Tetrahedron 42 (1986), 2831) and thermal or photochemical fragmentation of peroxides (DE-A 20 26 056) or other derivatives (DE-A 41 15 182).

A particularly advantageous preparation of lactones II and III involves fragmenting the readily producible 12-hydroperoxy-13-oxabicyclo[10.3.0]pentadecane or 12-hydroperoxy-14-methyl-oxabicyclo[10.3.0]pentadecane with the addition of copper(II) and iron(II) salts in accordance with a process described by S. L. Schreiber et al. (J. Amer. Chem. Soc. 102 (1980), 6163) for the synthesis of recifeiolides.

The excellent olfactory properties have to date not been recognized either for the unsaturated lactones or for the saturated lactones. Indeed, lactone III (R=H) is described in the literature as having a sandalwood scent (Helv. Chim. Acta 78, 440 (1995)), although the products prepared by ourselves have a distinctly soft long-lasting musk and nitromusk character. We also found this to be the case for the isomeric compounds of the lactones II.

The macrocyclic lactones to be used according to the invention are specifically:

11-cis-tetradecen-14,1-olide
11-trans-tetradecen-14,1-olide
12-cis-tetradecen-14,1-olide
12-trans-tetradecen-14,1-olide
11-cis-14-methyl-tetradecen-14,1-olide
11-trans-14-methyl-tetradecen-14,1-olide
12-cis- 14-methyl-tetradecen- 14,1-olide
12-trans-14-methyl-tetradecen-14,1-olide
14,1-tetradecanolide
14-methyl-tetradecanolide-14,1.

Due to their excellent olfactory properties, the fragrances listed may be used individually or as mixtures in a wide variety of fragrance compositions. It has been shown that skillful mixing of these compounds with other ingredients can enhance fragrance notes. Another important characteristic of these compounds is their ability, when mixed with other ingredients, to "round off" and "intensify the initial scent" of fragrance compositions. "Rounding off" is a property of a fragrance composition which ensures that a harmonious scent impression is achieved when the individual components are combined, and that none of the individual fragrance components stands out from the bouquet of the composition. The term "intensity of initial scent" refers to the first impression which a fragrance composition evokes, i.e. to the characterization of the initial scent. As is known, it is essential when formulating compositions to achieve a good balance between "rounding off" and "intensity of the initial scent".

Lactones II and III permit the formulation of novel types of interesting compositions. Amounts of from 8–15% by weight of lactone, based on the composition, are preferred.

As well as being used in fine perfumery, such compositions can be used to perfume cosmetics, such as creams, lotions, aerosols, toilet soaps, industrial articles, detergents, fabric conditioners, disinfectants and textile treatment agents. For this purpose, 1–5% by weight, based on the substrate to be perfumed, are preferred.

EXAMPLES

1. Preparation of the Hydroperoxide

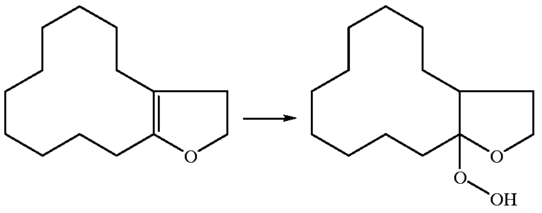

(V) (IV)

A 2 litre three-necked flask is charged with 880 g of acetic acid, and 154 g of the enol ether V are added at 0° C. A mixture of 147 g of 30 percent perhydrol and 36 g of semi-conc. sulphuric acid is then metered in over the course of 30 min, after which the mixture is stirred for a further 15 min at the given temperature, and the precipitated product is filtered off. The precipitate is washed with 250 ml of 50 percent acetic acid and with 5×400 ml of water until neutral. The white crystals are suspended in 500 g of methyl tert-butyl ether (MTBE) and the water phase which is deposited is removed, giving 150 g of the hydroperoxide IV.

2. Preparation of the Cyclotetradecenolide

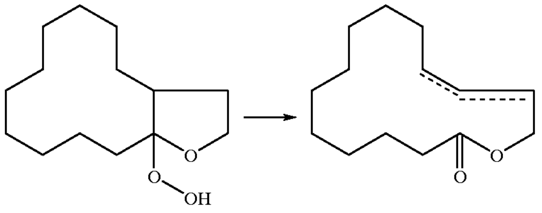

(IV) (IIa)

A 6 liter three-necked flask is charged with a solution of 114 g of copper(II) acetate in 2250 g of water, and a suspension of 150 g of IV in 500 g (MTBE) is added with stirring. A solution of 172 g of iron(II) sulphate in 760 g of water is then metered in at RT over the course of 15 min, after which the mixture is stirred for a further 30 min and adjusted to pH 1 using 550 g of 2 N hydrochloric acid. The product is then extracted with 3×1500 g of MTBE, the organic phase is washed with bicarbonate until neutral and distilled, giving 107 g of the cyclotetradecenolide IIa as an isomeric mixture.

3. Preparation of the Cyclotetradecanolide

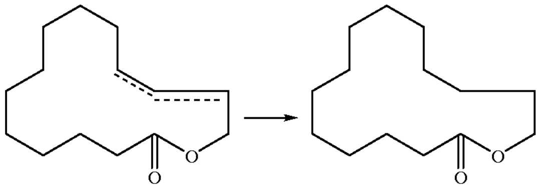

(IIa) (IIIa)

52g of the unsaturated lactone IIa are hydrogenated in isopropanolic solution with the addition of Pd/C catalyst at 40° C. After the catalyst has been filtered off, the solvent is removed and the residue which remains is distilled, giving 42 g of the cyclotetradecanolide IIIa.

4. Preparation of a Perfume Oil

| Ingredients | Amount in g |
|---|---|
| Bergamot oil | 100 |
| Vertocitral | 2 |
| Hexenyl salicylate, cis-3 | 13 |
| Profarnesol | 10 |
| Isoananate | 5 |
| Hexahydroiraldein | 25 |
| Hedion | 200 |
| Indole | 5 |
| Linalool | 150 |
| Mandarin oil, Italian | 50 |
| Octalactone, gamma | 5 |
| Phenoxanol | 50 |
| Rosaphen | 100 |
| Boisanol | 100 |
| Sandolen | 30 |
| Coumarin | 10 |
| Vanillin | 10 |
| Compound IIIa | 135 |
| Total | 1000 |

The addition of 8–15% of the substance IIIa gives this sweet oriental composition an enhanced base note as a result of a musk impression which can best be characterized as nitromusk.

We claim:

1. A musk fragrance composition comprising a compound having the following formula:

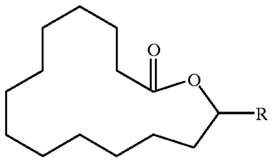

wherein R is hydrogen or methyl, and a carrier.

2. The musk fragrance of claim 1 wherein the compound is present in the composition at between 8 and 12 percent by weight.

3. A musk perfume oil comprising a compound having the following formula:

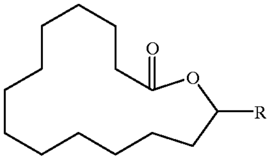
wherein R is hydrogen.
4. A method of enhancing a fragrance with a musk note comprising the step of adding a compound having the following formula to the fragrance:
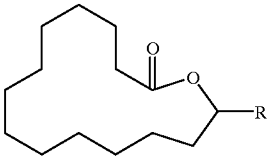
wherein R is hydrogen or methyl.
* * * * *

UNITED STATES PATENT AND TRADEMARK OFFICE

CERTIFICATE OF CORRECTION

PATENT NO. : 6,008,185 Page 1 of 1
DATED : December 28, 1999
INVENTOR(S) : Heinz-Jürgen Bertram et al.

It is certified that error appears in the above-identified patent and that said Letters Patent is hereby corrected as shown below:

Claim 2, line 2, delete "12 percent" and substitute -- 15 percent -- in its place.

Signed and Sealed this

Fourteenth Day of August, 2001

*Attest:*

Nicholas P. Godici

NICHOLAS P. GODICI

*Attesting Officer* *Acting Director of the United States Patent and Trademark Office*